United States Patent [19]

Tsuk

[11] Patent Number: 4,933,184

[45] Date of Patent: Jun. 12, 1990

[54] MENTHOL ENHANCEMENT OF TRANSDERMAL DRUG DELIVERY

[75] Inventor: Andrew G. Tsuk, Arlington, Mass.

[73] Assignee: American Home Products Corp. (Del), New York, N.Y.

[21] Appl. No.: 34,803

[22] Filed: Apr. 3, 1987

Related U.S. Application Data

[63] Continuation-in-part of Ser. No. 564,654, Dec. 22, 1983, abandoned.

[51] Int. Cl.$^5$ .................... A61K 9/06; A61F 13/00; A61L 15/03
[52] U.S. Cl. .................... 424/449; 514/946; 514/947
[58] Field of Search ............... 424/449; 514/946, 947

[56] References Cited

U.S. PATENT DOCUMENTS

| | | | |
|---|---|---|---|
| 3,880,996 | 4/1975 | Fisher | 516/63 |
| 3,891,757 | 6/1975 | Higuchi | 514/178 |
| 3,968,245 | 6/1976 | Higuchi | 514/772 |
| 3,989,816 | 11/1976 | Rajadhyaksha | 424/274 |
| 4,178,373 | 12/1979 | Klein et al. | 514/1 |
| 4,261,982 | 4/1981 | Luedders et al. | 514/29 |
| 4,316,887 | 2/1982 | Kamishita et al. | 424/78 |
| 4,353,896 | 10/1982 | Levy | 424/195.1 |
| 4,362,737 | 12/1982 | Schafer et al. | 514/399 |
| 4,405,616 | 9/1983 | Rajadhyaksha | 424/244 |
| 4,440,777 | 4/1984 | Zupan | 424/180 |
| 4,440,778 | 4/1984 | Matsui | 424/274 |
| 4,455,146 | 6/1984 | Noda et al. | 604/897 |
| 4,474,753 | 10/1984 | Haslam et al. | 514/912 |
| 4,474,798 | 10/1984 | Inagi | 424/274 |
| 4,485,087 | 11/1984 | Otsuka et al. | 424/28 |
| 4,500,511 | 2/1985 | Kigasawa et al. | 424/81 |
| 4,592,753 | 6/1986 | Panoz | 424/449 |
| 4,661,441 | 4/1987 | Kajiwara | 430/555 |
| 4,675,009 | 6/1987 | Hymes et al. | 424/448 |
| 4,695,465 | 9/1987 | Kigasawa | 424/449 |
| 4,714,655 | 12/1987 | Burdolol et al. | 424/448 |
| 4,719,239 | 1/1988 | Muller | 514/785 |
| 4,731,241 | 3/1988 | Yamada | 514/227 |
| 4,738,984 | 4/1984 | Parker | 514/473 |
| 4,743,249 | 5/1988 | Loveland | 424/447 |
| 4,764,381 | 8/1988 | Bodor | 424/449 |
| 4,800,197 | 1/1989 | Kowcz | 514/162 |
| 4,801,458 | 1/1989 | Hidaka | 424/443 |
| 4,820,525 | 4/1989 | Leonard . | |

FOREIGN PATENT DOCUMENTS

83/03548 10/1983 PCT Int'l Appl. .

OTHER PUBLICATIONS

Martindale Extra Pharmacopoeia 28th Ed. (1982) pp. 672, 673, 675, 351-352 "Cajuput Oil" Cineole Eucalyptus Oil Camphor and Menthol.

Derwent Abstract of JPN 58004713 (1/83) Yugioku Yakohin Koey.

Derwent Abstract of Ger. Off. 3231400 (3/83) Kawamura Inst. (Aurika).

*Primary Examiner*—Shep K. Rose
*Attorney, Agent, or Firm*—Adley F. Mandel

[57] ABSTRACT

Disclosed herein are compositions and methods for enhancing the transdermal delivery of physiologically active agents across mammalian skin or membranes and which comprise a percutaneous transfer enhancing amount of menthol and a drug.

16 Claims, No Drawings

MENTHOL ENHANCEMENT OF TRANSDERMAL DRUG DELIVERY

This application is a continuation-in-part of application Ser. No. 564,654, filed Dec. 22, 1983, now abandoned.

BACKGROUND OF THE INVENTION

The development of new or improved dosage forms and delivery means for physiologically active agents has been and will continue to be the subject of research for both existing and novel drugs. In too many instances a particular drug dosage provides for more drug than is actually required to produce an efficacious and safe therapeutic blood level free from side effects. The reasons for such theoretically excessive doses are many and include, inter alia, the mode of administration, the metabolism of the drug in the gastrointestinal tract, the absolute absorption (bioavailability) of the drugs and the situs of absorption. In another aspect the use of sustained release dosage forms and delivery means has increased to further both paint compliance and convenience.

More recently, investigations respecting transdermal drug delivery systems have increased resulting in a number of commercially available products especially for the administration of nitroglycerine. These latter systems apparently provide the advantages inherent in sustained delivery dosage forms and avoid the problems of a drug's rapid metabolism upon oral administration. At the same time less drug, although equally efficacious therapeutically to a greater amount orally administered, is ingested or absorbed by the patient. Nevertheless, the feasibility, the success and potential of such transdermal systems have heretofore been limited to drugs that are efficacious at lower dose levels and/or have relatively limited water solubility. The explanation for such limitations arise from the formidable barrier provided by the external layer(s) of animal skin and membrane tissues and the limited body areas which are usefully available for application of such transdermal dosage forms.

Various efforts have been pursued to expand the availability of transdermal delivery to more drugs and overcome the barrier presented by animal skin and membrane. Most such efforts, at least those employing transdermal drug delivery devices, have concentrated on increasing the diffusion of the drug from the device into and through the aforementioned barriers. Other efforts have been more specifically targeted at improving the permeability characteristics or percutaneous absorption capacity of the barrier itself. While some of these latter efforts have reportedly shown some success, the agents employed frequently have caused undesirable systemic side effects as well as tissue damage and irritation at the situs of application.

Agents reported to act as penetration enhancers for transdermal drug delivery include dimethylsulfoxide, disclosed in U.S. Pat. No. 3,551,554; combinations of sucrose fatty acid esters with a sulfoxide or phosphoric oxide, disclosed in U.S. Pat. Nos. 3,896,238; 3,952,099 and 4,046,886; and the 1-substituted azacycloalkan-2-ones which are the subject of U.S. Pat. Nos. 3,989,816; 4,316,893 and 4,405,616.

SUMMARY OF THE INVENTION

The present invention relates to compositions useful for the transdermal delivery of physiologically active agents to mammals. More particularly, this invention relates to compositions and methods which enhance the percutaneous transfer of topically applied, systemically active drugs and particularly such drugs which have aqueous solubility or which can be made water soluble by the use of derivatives, or in composition, through selection of appropriate pH, buffers, solvents and excipients. Thus the composition of this invention comprises at least one systemically active, water soluble or solubilizable drug, a percutaneous transfer enhancing amount of menthol and a pharamceutically acceptable vehicle in which the menthol is soluble.

In a further aspect, the invention relates to a method for enhancing the transfer of physiologically active agents into and through mammalian skin and membranes. The method comprises topically applying or administering to substantially the same section of the mammalian skin or membrane an effective amount of a systemically active, water soluble or solubilizable drug, a percutaneous transfer enhancing amount of menthol and a pharmaceutically acceptable vehicle.

Still a further embodiment of this invention resides in a unit dosage form for transdermal delivery of physiologically active agents to mammals. The dosage form comprises an effective amount of a systemically active, water soluble or solubilizable drug comprised within at least one drug reservoir means; a percutaneous transfer enhancing amount of menthol comprised within menthol delivery means; menthol solubilizing means and securing means for attaching the dosage form to a mammal.

DETAILED DESCRIPTION OF THE INVENTION

Menthol is a secondary alcohol obtained naturally from peppermint or other mint oils or prepared synthetically. Menthol has many uses as an ingredient in various medicinal preparations due to its analgesic, local anesthetic and counter irritant properties. It has now been found that menthol acts to enhance the percutaneous transfer of systemically active drugs in mammal. In this invention, the terms "physiologically active agent(s)" or "drug(s)" do not include either menthol or indomethacin in their definition.

Thus, this invention provides a topical composition for the transdermal and sustained delivery of physiologically active agents to mammals, said composition comprising an effective amount of a systemically active, water soluble or solubilizable drug, a percutaneous transfer enhancing amount of menthol and a pharmaceutically acceptable vehicle comprising at least one pharmaceutically acceptable solvent or solubilizer for said menthol.

In this invention the effective amount of drug will mean that amount of drug needed to produce a therapeutic dose following its transdermal administration. That amount will vary, depending, among other factors, on the physiological effect desired, the frequency of administration, drug and intradermal metabolism, drug half-life and the amount of menthol and perhaps other percutaneous transfer enhancers employed in the composition.

As stated, a percutaneous transfer enhancing amount of menthol is comprised in the composition. This amount for most drugs, generally ranges from about 4 to about 16 percent by weight of the composition.

The composition of the invention will further include a pharmaceutically acceptable vehicle containing at least one pharmaceutically acceptable solvent or solubilizer for said menthol. The vehicle in preferred compositions will also contain at least one pharmaceutically acceptable solvent which is a solvent or solubilizer for the drug. The respective solvents or solubilizers for the drug and menthol of this invention may be the same or different. In either case it is preferable that the solvents or solubilizers for each the drug and menthol, in the amounts employed, are at least partially soluble or miscible with each other. Most preferably, the solvents or solubilizers for each the drug and the menthol will, in the amounts employed, be wholly soluble or miscible with each other. The pharmaceutically acceptable vehicle may also contain other pharmaceutically acceptable excipients useful for formulating topical pharmaceutical compositions including buffers, neutralizing agents, pH modifiers, viscosity building or controlling agents, gel forming agents, emulsifiers, surfactants, polymers and the like.

The method and composition of this invention generally provide at least two fold enhancement of the delivery of water solubilizable drugs and five fold enhancement of the delivery of water soluble drugs, at least in in vitro models, and, preferably three fold and ten fold enhancement respectively.

Examples of solvents or solubilizers which may comprise the pharmaceutically acceptable vehicle of this invention include one or more of materials such as glycerin, propylene glycol, isopropanol, ethanol, a variety of polyethylene glycols, block copolymers of ethylene glycol and propylene glycol, acetylated monoglycerides, lanolin, mineral oil, water, aqueous buffers and the like.

Examples of systemically active drugs or their salts, some of which are also locally active, include:
Coronary vasodilators such as isosorbide dinitrate;
Corticoids such as hydrocortisone;
Analgesics and Antiinflammatory agents such as ibuprofen, etodolac, pemodolac and ketoprofen but not indomethacin;
Antidiabetics such as chlorpropamide;
Aldose reductase inhibitors such as tolrestat;
Bronchodilators such as albuterol;
Antihistamines such as chlorpheniramine;
Decongestants such as phenylpropanolamine;
Estrogens and progestogens including those of natural or synthetic orgin such as estradiol, norgesterel, conjugated estrogens such as PREMARIN, and medroxyprogesterone;
Tranquilizers and Hypnotics such as diazepam, temazepam, triazolam and alprazolam;
Beta blockers such as propanolol, cetamolol and atenolol;
Cerebral Melabolic activators, vasodilators and cognition enhancers such as vinpocetine;
Cardiotonics such as pelrinone and digoxin;
Peptide hormones such as insulin and somatostatin;
Agonists such as nicotine;
Lipid, cholesterol and triglyceride affecting agents such as acifran;
Other antihypertensive and calcium control agents.

A preferred group of drugs are those selected from the group consisting of etodolac, chlorpheniramine, propanolol, estrogens, progestogens and their pharmeceutically acceptable salts.

Another preferred group of drugs are those selected from the group consisting of cetamolol, acifran, phenylpropanolamine, ibuprofen, nicotine, diazepam, digoxin, insulin, somatostatin, isosorbide dinitrate, vinpocetine, pelrinone, hydrocortisone and their pharmaceutically acceptable salts.

In some cases, it is also desirable that the method or composition of the invention utilize the drug and its pharmaceutically acceptable salt together.

The composition of this invention for application to mammalian skin or membrane may take various forms including creams, lotions, gels, ointments, suppositories, sprays, aerosols and the like.

In another embodiment, the invention includes a method for treating mammals in need of treatment with systemically active agents by the transdermal administration of said agents sequentially or in combination with a percutaneous transfer enhancing amount of menthol. The method is effected by topically administering to substantially the same section of mammalian skin or membrane an effective amount of a systemically active, water soluble or solubilizable drug, a percutaneous transfer enhancing amount of menthol and a pharmaceutically acceptable vehicle. Thus, the method of the invention may also be employed as referred to hereinabove in the Summary of the Invention as a method for enhancing the transfer of physiologically active agents through mammalian skin and membranes. In either event the method may be realized through administration of the composition of the invention, a unit transdermal dosage form comprising the composition of the invention, or through sequential administration of the percutaneous transfer agent and drug of this invention via direct application to said mammal or via the unit transdermal dosage form of this invention comprising the same or different means for delivery of each of said percutaneous transfer agent and said drug.

The unit dosage form of this invention as hereinbefore described comprises an effective amount of a systemically active water soluble or solubilizable drug comprised within at least one drug reservoir means. Said drug reservoir means may take various forms such as pads or sponges impregnated with drug, a polymeric matrix containing the drug or composition of the drug, a gel formulation (or other formulation having some structural integrity) of the drug, a composition or solution of the drug within a walled container permeable to the drug and available to the skin or membrane of the mammal, a multiplicity of distinct microreservoir compartments containing the drug or drug composition within or homogenously throughout each microreservoir, layers of reservoirs and multiple variants of any of these enumerated and other drug reservoir presentations.

The unit dosage form, as with the other embodiments of this invention, further comprises a percutaneous transfer enhancing amount of menthol. In the unit dosage form, the menthol will be comprised within menthol delivery means which means can be selected from any of the described drug reservoir means, distinct menthol reservoir means and integral menthol reservoir means. Integral menthol reservoir means is defined to include the provision of the menthol together with the securing means, as for example in an adhesive layer.

Menthol solubilizing means and securing means for attaching or maintaining contact of the dosage form to a mammal are also comprised by the unit dosage form of the invention. The menthol solubilizing means comprise a pharmaceutically acceptable vehicle in which the menthol is soluble or solubilizable and which further is also either a solvent for the drug or is miscible with the drug or drug composition. Thus the menthol solubilizing means may be formulated with any of the menthol, the drug and/or in a distinct reservoir or depot within the unit dosage of the invention, so long as the menthol is soluble or made soluble therein and the drug or drug composition is soluble or miscible therewith prior to transfer through the skin or membrane of the mammal. The securing means will be selected from adhesives, belts such as those with "velcro" fittings, elastic bands or such other devices which are capable of securely attaching the unit dosage to the mammalian subject.

The invention is further illustrated by the following examples.

In examples 1-4; in-vitro percutaneous transfer tests with nude mouse skins were performed as follows; A piece of freshly excised nude mouse skin was mounted across a 6 $cm^2$ opening of a diffusion cell. The test formulation was first impregnated into 1-inch diameter circles of a thin non-woven rayon fabric usually in amounts representing about 20 mg or more per $cm^2$ of skin. The impregnated fabric was applied to the outside or epidermal side of the skin while the inside or tissue side of the skin was exposed to an aerated and stirred volume of Ringer's injection fluid maintained at about 37° C. Samples were taken at intervals from the stirred solution and assayed for drug content. The calculated total amount of percutaneously transferred drug is expressed as mg drug per $cm^2$ of exposed skin.

EXAMPLE 1

The following formulations containing propanolol hydrochloride were prepared:

|  | percent by weight | |
|---|---|---|
|  | A | B |
| Propanolol hydrochloride | 55.6 | 29.6 |
| Glycerol | 26.6 | 47.8 |
| Propylene glycol | — | 8.1 |
| Menthol | 17.8 | — |
| n-Decylmethylsulfoxide | — | 3.8 |
| sucrose stearate | — | 10.7 |

The formulation A mixture became a clear homogenous liquid upon heating but solidified amidst crystallization upon cooling. Formulation B was prepared according to methods described in U.S. Pat. Nos. 3,952,099 and 4,046,886. Two circles of non-woven fabric were impregnated with each formulation (designated A1, A2 and B1, B2 respectively) and tested for percutaneous drug transfer across nude mouse skin.

|  | A1 | A2 | B1 | B2 |
|---|---|---|---|---|
| Amount of drug present in formulation applied to epidermal surface (mg/$cm^2$) | 10.95 | 8.83 | 5.17 | 5.83 |
| Amount of drug passing across skin (mg/$cm^2$) after |  |  |  |  |
| 2 hours | 0.01 | 0.003 | 0.004 | 0.005 |
| 4 hours | 1.05 | 0.20 | 0.02 | 0.03 |
| 6 hours | 1.49 | 0.91 | 0.06 | 0.06 |
| 9 hours | 8.27 | 2.83 | 0.18 | 0.12 |
| 12 hours | 8.83 | 3.48 | 0.37 | 0.18 |
| 22 hours | 9.20 | 4.93 | 1.31 | 0.50 |

The menthol formulation caused much higher transfer than the reference formulation. The difference was larger than the skin-to-skin variation seen in the duplicate runs.

EXAMPLE 2

Formulations containing conjugated estrogens were prepared. A purified and dried concentrate of Conjugated Equine Estrogens was used, which contained per gram, 324 mg of conjugated estrogens when assayed according to the methods specified in the XX. edition of the U.S. Pharmacopeia. The major components of this mixture of natural estrogens are sodium estrone sulfate (about 54%), sodium equilin sulfate (about 29%), and sodium dihydroequilin sulfate (about 13%). The formulation ingredients, as given below in percentages by weight, were combined, then warmed and stirred to give hazy amber solutions.

| Formulation | C | D | E |
|---|---|---|---|
| Dried concentrate of Conjugated Estrogens | 4.1 | 4.1 | 5.0 |
| Propylene glycol | 64.3 | 64.1 | 64.9 |
| Isopropanol | 16.1 | 12.0 | 8.1 |
| Water | 15.5 | 15.8 | 13.9 |
| Menthol | 0 | 4.0 | 8.1 |

Two circles of nonwoven fabric were impregnated with each formulation, so as to contain 2-3 mg of conjugated estrogens. These were applied to nude mouse skins (6 $cm^2$ exposed surface) for transdermal penetration tests. The average of duplicate tests is given below, in units of $\mu g$ of transferred estrogen per $cm^2$ of exposed skin surface.

|  | C | D | E |
|---|---|---|---|
| Sodium estrone sulfate ($\mu g/cm^2$) passing across skin after |  |  |  |
| 2 hours | 0 | 0 | 2 |
| 4 hours | 0 | 1 | 32 |
| 6 hours | 0 | 7 | 101 |
| 13 hours | 0 | 46 | 164 |
| 22 hours | 0 | 99 | 223 |
| Sodium equilin sulfate ($\mu g/cm^2$) passing across skin after |  |  |  |
| 2 hours | 0 | 0 | 0.6 |
| 4 hours | 0 | 0.2 | 13 |
| 6 hours | 0 | 3 | 44 |
| 13 hours | 0 | 19 | 84 |
| 22 hours | 0 | 44 | 103 |
| Sodium dihydroequilin sulfate ($\mu g/cm^2$) passing across skin after |  |  |  |
| 2 hours | 0 | 0 | 0.3 |
| 4 hours | 0 | 0.2 | 7 |
| 6 hours | 0 | 2 | 25 |
| 13 hours | 0 | 11 | 45 |
| 22 hours | 0 | 28 | 62 |

The formulation without menthol did not allow the passage of detectable amounts of estrogen across the skin. The two menthol containing formulations, however, caused the transfer of large amounts of estrogens. All three of the major constituents penetrated the skin, in proportions essentially equal to the original mixture composition.

EXAMPLE 3

Formulations containing etodolac, 1,8-diethyl-1,3,4,9-tetrahydropyrano[3,4-b]indole-1-acetic acid, a non-steroidal antiinflammatory, analgesic agent were prepared with and without 5% menthol in a glycerol/propylene glycol vehicle. The agent, sparingly soluble in water, but solubilized by this vehicle demonstrated about a three fold increase in percutaneous transfer in the presence of menthol. In other experiments, wherein the aqueous solubility of the etodolac were increased via the employment of buffers and/or alkalizing agents the enhancing effect of menthol was even more pronounced in the nude mouse skin studies.

EXAMPLE 4

Formulation containing 17-β-estradiol (a non-water soluble estrogen) in lipophilic vehicles with and without menthol demonstrated no significant differences in percutaneous transfer. However, when employing 17-β-estradiol-3-sodium sulfate a water soluble derivative of said estrogen in hydrophilic vehicles, formulations containing menthol demonstrated significantly higher flux rates in the nude mouse skin studies.

EXAMPLE 5

In this experiment the following formulations with and without menthol were evaluated in male albino rats.

|  | weight percent | |
|---|---|---|
|  | A | B |
| Propanolol hydrochloride | 18.02 | 17.98 |
| Glycerin | 54.10 | 63.88 |
| Isopropanol | 17.84 | 18.14 |
| Menthol | 10.04 | — |

The above formulations were impregnated on circular, cotton matrix patches, each patch having a diameter of 3 cm and containing 0.3 g of test formulation. The patches were applied to a shaved area on the backs of the animals and covered (secured) with adhesive tape. Blood samples were obtained twice (for each rat) from ten rats in each of two treatment groups at different time points.

The results at the indicated time points are as follows, the plasma level mean at each time point representing the average of two animals.

|  | Mean in ng/ml | |
|---|---|---|
| Time (Hours) | A | B |
| 1 | 0.8 | 5.5 |
| 2 | 165.5 | 6.0 |
| 3 | 140.0 | 9.5 |
| 4 | 115.5 | 9.0 |
| 6 | 457.0 | 4.5 |
| 8 | 491.0 | 0.8 |
| 12 | 922.0 | 4.5 |
| 16 | 1317.0 | 11.5 |
| 24 | 628.0 | 6.5 |
| 32 | 73.5 | 1.8 |

EXAMPLE 6

In these experiments, the indicated test formulation was impregnated into non woven rayon patches (reservoirs). The patches (about 0.79 cm$^2$) were then applied to the strateum corneum side of the indicated test skin and maintained thereat by application of an occlusive backing. The test skin had been previously mounted across the opening of diffusion cell which contained phosphate buffer (pH 7.4) maintained at 32° C. as the receiving fluid, stirred past the skin. Sample volumes removed for assay were replaced by an equal volume of fresh phosphate buffer.

The units employed in the formulation are expressed as percent w/w (weight/weight). Other units of measurement not specifically expressed are:

Flux=steady state (mcg.hr.$^{-1}$ cm$^{-2}$)
Flux Ratio=Enhanced Flux/Unenhanced Flux
[m]=Menthol concentration (% w/w) of formulation
AD=Amount diffused (mcg.)
% D=Percent diffused I Experiment—Albuterol
Test Species—Mouse
Skin Type—Whole skin
Drug Type—Bronchodilator; Study Time—24 hours

| Formulations | A | B | C | D | E | F |
|---|---|---|---|---|---|---|
| Menthol | — | — | 5.14 | 9.88 | 9.97 | 15.11 |
| 1-Methyl-2-pyrrolidone | 23.85 | 23.78 | 22.48 | 21.75 | 21.20 | 20.14 |
| Albuterol | 5.07 | 5.01 | 5.04 | 4.86 | 4.90 | 4.96 |
| Diethylene Glycol Monoethylether | 71.08 | 71.21 | 67.35 | 63.51 | 63.93 | 59.79 |

| | | Results - Albuterol | | | |
|---|---|---|---|---|---|
| | | Total | | | Flux |
| Formulation | [m] | AD | % D | Flux | Ratio |
| A-1 | 0 | 393.32 | 35.11 | 31.67 | |
| A-2 | 0 | 267.30 | 27.27 | 23.91 | |
| Avg. | | 330.31 | 31.19 | 27.79 | |
| B-1 | 0 | 408.82 | 43.18 | 40.56 | |
| B-2 | 0 | 285.32 | 29.97 | 26.65 | |
| Avg. | | 338.69 | 33.88 | 30.70 (A + B) | |
| C-1 | 5.14 | 821.75 | 70.28 | 74.57 | |
| C-2 | 5.14 | 992.89 | 89.96 | 103.08 | |
| Avg. | | 907.32 | 80.12 | 88.82 | 2.89 |
| D-1 | 9.88 | 991.88 | 92.35 | 150.69 | |
| D-2 | 9.88 | 950.73 | 89.33 | 112.35 | |
| Avg. | | 971.30 | 90.84 | 131.52 | 4.28 |
| E-1 | 9.97 | 1036.07 | 99.27 | 128.09 | |
| E-2 | 9.97 | 1000.62 | 95.87 | 107.18 | |
| Avg. | | 1018.34 | 97.57 | 117.64 | 3.83 |
| F-1 | 15.11 | 969.95 | 90.12 | 126.49 | |
| F-2 | 15.11 | 1004.49 | 93.76 | 118.12 | |
| Avg. | | 987.22 | 91.94 | 122.30 | 3.98 |

II Experiment—Albuterol Sulfate
Test Species—Mouse
Skin Type—Whole skin
Drug Type—Bronchodilator; Study Time—24 hours

| Formulations | A | B | C |
|---|---|---|---|
| Menthol | — | 5.00 | 9.75 |
| Water | 24.30 | 23.09 | 22.67 |
| Albuterol Sulfate | 5.01 | 4.91 | 4.91 |
| Diethylene Glycol Monoethylether | 70.69 | 67.00 | 62.67 |

| | | Results - Albuterol Sulfate | | | |
|---|---|---|---|---|---|
| | | Total | | | Flux |
| Formulation | [m] | AD | % D | Flux | Ratio |
| A-1 | 0 | 141.40 | 12.17 | 11.69 | |
| A-2 | 0 | 99.91 | 8.86 | 8.19 | |
| A-3 | 0 | 62.24 | 5.78 | 5.46 | |
| Avg. | | 101.18 | 8.94 | 8.45 | |
| B-1 | 5.00 | 792.90 | 74.45 | 55.45 | |
| B-2 | 5.00 | 1039.98 | 92.93 | 85.34 | |
| Avg. | | 916.44 | 83.69 | 70.44 | 8.34 |
| C-1 | 9.75 | 931.12 | 86.61 | 64.05 | |
| C-2 | 9.75 | 780.92 | 75.74 | 57.43 | |

-continued

| Results - Albuterol Sulfate | | | | | |
|---|---|---|---|---|---|
| | | Total | | | Flux |
| Formulation | [m] | AD | % D | Flux | Ratio |
| Avg. | | 856.02 | 81.18 | 60.74 | 7.19 |

III Experiment—Hydrocortisone
Test Species—Mouse
Skin Type—Whole skin
Drug Type—Glucocorticoid; Study Time—21 hours

| Formulations | A | B |
|---|---|---|
| Menthol | — | 9.64 |
| 1-methyl-2-pyrrolidone | 80.12 | 70.81 |
| Hydrocortisone (radiolabeled) | 19.88 | 19.55 |

| Results - Hydrocortisone | | | | | |
|---|---|---|---|---|---|
| | | Total | | | Flux |
| Formulation | [m] | AD | % D | Flux | Ratio |
| A-1 | 0 | 228.79 | 7.28 | 15.1 | |
| A-2 | 0 | 169.45 | 5.57 | 9.8 | |
| Avg. | | 199.12 | 6.42 | 12.4 | |
| B-1 | 9.64 | 319.60 | 11.12 | 36.50 | |
| B-2 | 9.64 | 464.28 | 14.66 | 35.21 | |
| Avg. | | 391.94 | 12.89 | 35.86 | 2.89 |

IV Experiment—17—β—Estradiol
Test Species—Cadaver
Skin Type—Dermatomed Epidermis (0.250 mm)
Drug Type—Estrogen; Study Time—47 hours

| Formulations | A | B | C | D |
|---|---|---|---|---|
| Menthol | 0 | 4.91 | 9.96 | 10.16 |
| 17-β-estradiol | 1.06 | 1.22 | 0.80 | 0.81 |
| Propylene Glycol | 98.94 | 93.87 | 89.24 | 89.03 |

| Results - 17-β-estradiol | | | | | |
|---|---|---|---|---|---|
| | | Total | | | Flux |
| Formulation | [m] | AD | % D | Flux | Ratio |
| A | 0 | 1.6 | 1.4 | 0.021 | |
| B-1 | 4.91 | 11.4 | 4.8 | 0.56 | |
| B-2 | 4.91 | 9.5 | 3.8 | 0.69 | |
| Avg. | | 10.45 | 4.3 | 0.62 | 29.52 |
| C-1 | 9.96 | 9.31 | 6.44 | 0.209 | |
| C-2 | 9.96 | 11.2 | 11.6 | 0.403 | |
| C-3 | 9.96 | 14.5 | 14.0 | 0.422 | |
| Avg. | | 11.00 | 10.68 | 0.345 | 16.43 |
| D-1 | 10.16 | 5.22 | 3.75 | 0.178 | |
| D-2 | 10.16 | 11.62 | 8.86 | 0.306 | |
| Avg. | | 8.42 | 6.30 | 0.24 | 11.43 |

V Experiment—Chloropropamide
Test Species—Mouse
Skin Type—Whole skin
Drug Type—Antidiabetic; Study Time—23 hours

| Formulations | A | B | C | D | E |
|---|---|---|---|---|---|
| Menthol | — | 1.15 | 4.99 | 10.06 | 15.00 |
| Chlorpropamide | 5.16 | 5.08 | 4.99 | 4.87 | 5.05 |
| N-methyl-2-pyrrolidone | 94.84 | 93.77 | 90.02 | 85.57 | 79.94 |

| Results - Chlorpropamide | | | | | |
|---|---|---|---|---|---|
| | | Total | | | Flux |
| Formulation | [m] | AD | % D | Flux | Ratio |
| A-1 | 0 | 117.67 | 11.42 | 7.32 | |
| A-2 | 0 | 127.49 | 12.38 | 9.10 | |
| Avg. | | 122.58 | 11.90 | 8.21 | |
| B-1 | 1.15 | 169.50 | 17.47 | 10.97 | |
| B-2 | 1.15 | 316.97 | 31.08 | 18.40 | |
| Avg. | | 243.24 | 24.28 | 14.68 | 1.79 |
| C-1 | 4.99 | 448.63 | 45.78 | 23.94 | |
| C-2 | 4.99 | 781.56 | 80.57 | 37.09 | |
| Avg. | | 615.10 | 63.18 | 30.52 | 3.72 |
| D-1 | 10.06 | 877.96 | 91.45 | 38.52 | |
| D-2 | 10.06 | 597.10 | 60.93 | 36.78 | |
| Avg. | | 757.53 | 76.19 | 37.65 | 4.59 |
| E-1 | 15.00 | 906.34 | 87.99 | 44.15 | |
| E-2 | 15.00 | 1053.18 | 96.62 | 39.31 | |
| Avg. | | 979.76 | 92.30 | 41.73 | 5.08 |

VI Experiment—Propranolol hydrochloride
Test Species—Cadaver
Skin Type—heat separated cadaver skin
Drug Type—beta blocker; Study Time—42 hours

| Formulations | A | B |
|---|---|---|
| Menthol | — | 9.19 |
| Propranolol HCl | 14.14 | 14.71 |
| Glycerin | 64.64 | 56.89 |
| Isopropanol | 21.23 | 19.22 |

| Results - Propranolol HCl | | | | | |
|---|---|---|---|---|---|
| | | Total | | | Flux |
| Formulation | [m] | AD | % D | Flux | Ratio |
| A-1 | 0 | 10.00 | 0.07 | 0.5 | |
| A-2 | 0 | 20.00 | 0.21 | 0.5 | |
| Avg. | | 15.00 | 0.14 | | |
| B-1 | 9.19 | 440.00 | 3.76 | 3.00 | |
| B-2 | 9.19 | 1890.00 | 16.50 | 20.00 | |
| Avg. | | 1165.00 | 10.13 | 11.50 | |

VII Experiment—Acebutolol HCl
Test Species—Mouse
Skin Type—Whole skin
Drug Type—Cardioselective beta blocker; Study Time—22 hours

| Formulations | A | B |
|---|---|---|
| Menthol | — | 10.18 |
| Acebutolol HCl | 29.85 | 29.28 |
| 4:1 Propylene Glycol:Water | 70.15 | 60.54 |

| Results - Acebutolol HCl | | | | | |
|---|---|---|---|---|---|
| | | Total | | | Flux |
| Formulation | [m] | AD | % D | Flux | Ratio |
| A-1 | 0 | 1050.86 | 2.29 | 12.00 | |
| A-2 | 0 | 523.39 | 1.10 | 6.00 | |
| Avg. | | 787.12 | 1.70 | 9.00 | |
| B-1 | 10.18 | 34554.72 | 72.09 | 480.00 | |
| B-2 | 10.18 | 33458.21 | 79.57 | 470.00 | |
| Avg. | | 34006.46 | 75.83 | 475.00 | 52.78 |

VIII Experiment—Tolrestat
Test Species—Mouse
Skin Type—Whole skin

Drug Type—Aldose Reductase Inhibitors; Study Time—23 hours

| Formulations | A | B |
|---|---|---|
| Menthol | — | 11.39 |
| Tolrestat | 14.77 | 15.29 |
| Propylene Glycol | 85.23 | 73.32 |

| | | Results - Tolrestat | | | |
|---|---|---|---|---|---|
| | | Total | | | Flux |
| Formulation | [m] | AD | % D | Flux | Ratio |
| A-1 | 0 | 420.00 | 1.63 | 6.00 | |
| A-2 | 0 | 610.00 | 2.34 | 6.00 | |
| Avg. | | 515.00 | 1.98 | 6.00 | |
| B-1 | 11.39 | 13770.00 | 51.31 | 220.00 | |
| B-2 | 11.39 | 7620.00 | 28.33 | 100.00 | |
| Avg. | | 10695.00 | 39.82 | 160.00 | 26.67 |

EXAMPLE 7

Formulations containing conjugated estrogens (Premarin ®) comparing the relative enhancement of menthol versus methyl salicylate were prepared:

| | percent by weight | |
|---|---|---|
| | A | B |
| Premarin ® | 8.4 | 8.4 |
| Propylene glycol | 60 | 60 |
| Ethanol | 16 | 16 |
| Water | 8 | 8 |
| Menthol | 8 | — |
| Methyl Salicylate | — | 8 |

In duplicate runs through cadaver skin of each of Formulations A and B, Formulation A with menthol was over 4 times as effective as Formulation B with methyl salicylate.

EXAMPLE 8

Formulations containing vinpocetine comparing the relative enhancement of menthol versus peppermint oil were prepared:

| | percent by weight | | | |
|---|---|---|---|---|
| | A | B | C | D |
| Vinpocetine | 5 | 5 | 5 | 5 |
| N-methyl-2-pyrrolidone | 95 | 85 | 90 | 85 |
| Peppermint Oil | — | 10 | — | — |
| Menthol | — | — | 5 | 10 |
| pH$_3$ | | | | |

In triplicate or duplicate runs (at different times) through mouse skin, Formulation B with peppermint oil, surprisingly, provided no enhancement over Formulation A. Formulations C and D provided on the order of 11 and 18 fold enhancement respectively over Formulation A.

EXAMPLE 9

Formulations containing propanolol hydrochloride and terpin hydrate, a compound with a structure similar to menthol were loaded onto non-woven patches and evaluated on hairless mouse skin. In duplicate runs conducted over 23 hours, the terpin hydrate containing formulation did not show any enhancing activity. The formulation tested was:

| | percent by weight |
|---|---|
| Terpin hydrate | 13 |
| Propranolol hydrochloride | 43.5 |
| Propylene glycol | 16 |
| Glycerol | 27 |

What is claimed is:

1. In a method for use in enhancing the transfer of physiologically active agents through mammalian skin and membranes to obtain sustained delivery of said agents by topical administration the improvement which consist essentially of topically applying to the same section of mammalian skin or membrane one or more compositions together consisting essentially of an effective amount of a systemically active, water soluble or solubilizable drug, a percutaneous transfer enhancing amount of method in an amount of about 4% to about 16% by weight of said composition(s), and a pharmaceutically acceptable vehicle.

2. The improved method of claim 1 wherein each of the drug and the menthol are administered sequentially.

3. The improved method of claim 1 wherein the drug and the menthol are administered to said mammal simultaneously.

4. The improved method of claim 1 which provides at least two fold enhancement of the delivery of water solubilizable drugs and five fold enhancement of the delivery of water soluble drugs when measured in in vitro models.

5. The improved method of claim 1 which provides at least three fold enhancement of the delivery of water solubilizable drugs and ten fold enhancement of the delivery of water soluble drugs when measured in in vitro models.

6. The improved of claim 1 wherein the menthol is soluble in said vehicle.

7. The improved method of claim 1 wherein the drug is selected from the group consisting of etodolac, chlorpheniramine, propranolol, estrogens, progestogens, and their pharmaceutically acceptable salts.

8. The improved method of claim 1 wherein the drug is selected from the group consisting of cetamolol, acifran, phenylpropanolamine, ibuprofen, nicotine, diazepam, digoxin, insulin, somatostatin, isosorbide dinitrate, vinpocetine, pelrinone, hydrocortisone, and their pharmaceutically acceptable salts.

9. In a topical composition for use the transdermal and sustained delivery of physiologically active agents to mammals the improvement comprising providing at least two fold enhancement of the delivery water solubilizable drugs and five fold enhancement of the delivery of water soluble drugs contained in the composition said composition consisting essentially of an effective amount of a systemically active, water soluble or solubilizable drug; a percutaneous transfer enhancing amount of menthol in an amount of about 4% to about 16% by weight of said composition; and a pharmaceutically acceptable vehicle comprising at least one pharmaceutically acceptable solvent or solubilizer for the menthol.

10. The improved composition of claim 9 in which the pharmaceutically acceptable vehicle further comprises at least one pharmaceutically acceptable solvent for the drug.

11. The improved composition of claim 10 in which the solvents for each of the drug and the menthol are, in the amounts employed, at least partially miscible with each other.

12. The improved composition of claim 10 in which each of the drug and the menthol are at least partially soluble in each solvent.

13. The improved composition of claim 9 comprising a water soluble drug which provides at least ten fold enhancement of the delivery of said drug.

14. The improved composition of claim 9 comprising a water solubilizable drug which provides at least five fold enhancement of the delivery of said drug.

15. The improved composition of claim 9 wherein the drug is selected from the group consisting of etodolac, chlorpheniramine, propranolol, estrogens, progestogens, and their pharmaceutically acceptable salts.

16. The improved composition of claim 9 wherein the drug is selected from the group consisting of cetamolol, acifran, phenylpropanolamine, ibuprofen, nicotine, diazepam, digoxin, insulin, somatostatin, isosorbide dinitrate, vinpocetine, pelrinone, hydrocortisone, and their pharmaceutically acceptable sales.

* * * * *